United States Patent
Berger et al.

(10) Patent No.: US 7,148,163 B2
(45) Date of Patent: Dec. 12, 2006

(54) GLASS AS SINTERING AID AND OPEN-PORE MOLDED BODY AND METHOD FOR MANUFACTURING SAME

(75) Inventors: Georg Berger, Zepernick (DE); Renate Gildenhaar, Berlin (DE); Andrea Spitzer, Berlin (DE)

(73) Assignee: BAM Bundesanstalt fur Materialforschung und-prufung, Berlin (DE)

( * ) Notice: Subject to any disclaimer, the term of this patent is extended or adjusted under 35 U.S.C. 154(b) by 260 days.

(21) Appl. No.: 10/689,220

(22) Filed: Oct. 20, 2003

(65) Prior Publication Data

US 2004/0235637 A1    Nov. 25, 2004

(30) Foreign Application Priority Data

Oct. 21, 2002  (DE)  ................. 102 49 626
Oct. 21, 2002  (DE)  ................. 102 61 992

(51) Int. Cl.
*C04B 35/447*  (2006.01)
*C03C 3/078*  (2006.01)

(52) U.S. Cl. .................. 501/1; 501/72; 623/23.56; 424/602

(58) Field of Classification Search .......... 501/1, 501/32, 72; 623/23.56; 424/602
See application file for complete search history.

(56) References Cited

U.S. PATENT DOCUMENTS

2004/0087429 A1* 5/2004 Ogawa et al. ................. 501/72
2004/0175430 A1* 9/2004 Berger et al. ................. 424/602
2004/0228927 A1* 11/2004 Berger et al. ................. 424/602
2005/0079226 A1* 4/2005 Gonda et al. ................. 424/602

FOREIGN PATENT DOCUMENTS

EP    0 237 043 B1    3/1987
EP    0 541 546 B1    11/1990

* cited by examiner

*Primary Examiner*—Karl Group
(74) *Attorney, Agent, or Firm*—Stephan A. Pendorf; Akerman Senterfitt

(57) ABSTRACT

The present invention relates to a glass used as a sintering aid for a resorbable molded body containing calcium phosphate as well as to a method for manufacturing said molded body. According to the invention, the material is β-tricalcium phosphate and the glass has a chemical composition of 68–78% by weight $SiO_2$, 5–12% by weight MgO and 12–27% by weight $Na_2O$. The aforesaid molded body is manufactured by melting said glass, grinding it until a grain size $D_{50}$ of 0.7–2 μm is achieved and mixing it with β-tricalcium phosphate having a grain size $D_{50}$ of 1–7.5 μm, giving the mixture the desired shape and producing the molded body by sintering said mixture at between 1,150 and 1,350° C., wherein the grain size of β-TCP must not be smaller than that of the glass.

2 Claims, No Drawings und METHOD
GLASS AS SINTERING AID AND OPEN-PORE MOLDED BODY AND METHOD FOR MANUFACTURING SAME

BACKGROUND OF THE INVENTION

1. Field of the Invention

The present invention relates to a glass used as a sintering aid for a resorbable moulded body containing calcium phosphate as well as to a method for manufacturing said moulded body.

2. Description of the Related Art

Inorganic bone replacement materials can be divided into resorbable and long-term stable materials. They are selected and used according to the specific medical indication. Materials based on tricalcium phosphates are state of the art as regards the use of resorbable products contributing to a direct contact of bones. In most cases, granulated materials having different grain sizes are used. There is the problem, however, that during biodegradation and the simultaneous growth of new bone tissue, the granules remaining in the bone defect which has been operated and filled with the granulated material are pressed against one another and prevent a complete dissolution of the bone replacement material. The aforesaid problem can be solved in different ways. One method consists in developing materials which can be resorbed more rapidly (e.g. EP 541564 B1), another one consists in providing the granulated materials with an inner porosity thus facilitating their dissolution once they have been pressed against one another (e.g. DE 19744809 C1).

In principle, the problem can also be solved by manufacturing an open-pore and at the same time large-pore moulded body. This can be done by pressing or isostatically pressing the starting material, subsequently sintering it and finally providing it with the pore structure by boring, etc. using various techniques (mechanically, using dry ice, etc.), by means of so-called free-form fabrication techniques or according to the known sponge impregnation technique with subsequent sintering (Schwartzwalder-Somers process).

The aforesaid solutions frequently have the disadvantage that the tricalcium phosphate to be used is not sintered to a sufficient degree and, as a result, the moulded bodies obtained are relatively unstable from a mechanical point of view.

SUMMARY OF THE INVENTION

The object of the invention is to decisively improve the sintering capability of materials containing calcium phosphate while maintaining or even improving the resorbability and biocompatibility of the moulded body manufactured from said materials.

According to the invention, a glass is provided which can be used as a sintering aid for a resorbable material containing calcium phosphate, the material being β-tricalcium phosphate and the glass having a chemical composition of 68–78% by weight $SiO_2$, 5–12% by weight MgO and 12–27% by weight $Na_2O$.

A glass having a chemical composition of 73–78% by weight $SiO_2$, 8–11% by weight MgO and 12–19% by weight $Na_2O$, particularly 74–75% by weight $SiO_2$, 8.5–10% by weight MgO and 14.5–17% by weight $Na_2O$, is particularly advantageous.

The glass makes up 0.5–15% by weight while tricalcium phosphate (TCP) makes up 85–99.5% by weight.

The components, i.e. TCP and glass as amorphous component, are produced separately, ground separately and then mixed, using a mill again, if necessary, the mixture is processed into a slurry comprising further additives which is then applied e.g. onto a polyurethane (PUR) sponge. Once the sponge has dried, it is subjected to a thermal treatment during which the sponge is burned completely and a moulded body is obtained which contains only one crystal phase made up of TCP according to X-ray diffractographic measurements.

As a result, moulded bodies are obtained which contain the following individual components up to a maximum amount in % by weight in the synthesized composition of:

CaO: 53.97
$P_2O_5$: 45.53
$SiO_2$: 11.40
$Na_2O$: 4.05
MgO: 1.8

The amounts of the components are selected such that they jointly make up max. 100% of the synthesized composition.

Surprisingly, it has been found that the 2-component variant described above yields the desired sintered product, whereas an immediate combination of all components does not support the sintering process as desired. Unless the separately produced amorphous glass phase is added, no solid structure is achieved by applying the TCP slurry onto a polyurethane sponge and sintering it, but parts of the sintered product crumble away.

Therefore, the invention also relates to a method for manufacturing a resorbable moulded body containing calcium phosphate, which method is characterized in that a glass consisting of 68–78% by weight $SiO_2$, 5–12% by weight MgO and 12–27% by weight $Na_2O$ is melted, ground until a grain size $D_{50}$ of 0.7–2 μm is achieved and mixed with β-tricalcium phosphate having a grain size $D_{50}$ of 1–7.5 μm, the mixture is given the desired shape in a known manner and the moulded body is produced by sintering said mixture at between 1,150 and 1,350° C., wherein the grain size of β-TCP must not be smaller than that of the glass.

Consequently, the invention also relates to an open-pore moulded body based on β-tricalcium phosphate, which moulded body is characterized by a composition (in % by weight) ranging from 46.1 to 54.0 CaO, 38.9 to 45.5 $P_2O_5$, 0.005 to 11.4 $SiO_2$, 0.001 to 4.05 $Na_2O$ and 0.0005 and 1.8 MgO and in that it comprises a crystalline phase consisting of β-tricalcium phosphate according to roentgenographic analyses. The requirements with regard to the β-TCP's purity conform to the ASTM F 1088-87 standard (re-approved in 1992).

The invention further relates to the aforesaid open-pore moulded body manufactured by separately producing β-tricalcium phosphate and a glass consisting of 68–78% by weight $SiO_2$, 5–12% by weight MgO and 12–27% by weight $Na_2O$, mixing 99.5–85% by weight β-tricalcium phosphate and 0.5–15% by weight glass, processing said mixture into a slurry in a usual manner, applying it onto an open-pore sponge, preferably an open-pore PUR sponge, and sintering it at between 1,150 and 1,350° C. to obtain the moulded body.

The glass used as an additive preferably makes up 1–10% by weight, advantageously 4–8%, particularly 5–7% by weight.

The invention is in no way limited to the exemplary embodiment described above, but other products whose composition varies within the range indicated hereinbefore and which have similar properties can be produced by the melting process as well.

The effect achieved decisively depends on that the amorphous component is finely ground, e.g. in an agitator bead mill, and its $D_{50}$ value is preferably smaller than that of tri-calcium phosphate and in any case clearly smaller than 1 μm.

The amorphous products used, which are obtained by a melting process, are relatively unstable from a chemical point of view thus contributing to the resorbability of the moulded body as a whole. Biocompatibility is ensured by the fact that the sintering aid contains nothing but physiological constituents. The only critical point is the slightly increased silicon content as blood or bone tissue only contain small amounts of silicon. However, the additional amount is very small relative to the moulded body as a whole. Recent specialist publications suggest that the osteoclasts' (cells decomposing bone tissue) activity can be stimulated thus enhancing the material's resorbability by thoroughly mixing all starting materials with silicon, in contrast to the 2-component method used in the invention. The aforesaid conclusion is based on the analysis of open-pore material mixtures consisting of Si-α-TCP and hydroxyapatite which had been produced using colloidal $SiO_2$ brines (Langstaff, S. et al.: Resorbable bioceramics based on stabilized CP. Part I: Rational design, sample preparation and materials characterization, Biomaterials 20 (1999)1727–1741; Part II: Evaluation of biological response, Biomaterials 22 (2001)135–150).

The material can be produced according to the Schwartzwalder-Somers process mentioned hereinbefore, in which a slurry is applied onto a PUR sponge and the sponge is then burnt completely.

Another method which can be used in an advantageous manner for the production of the material according to the invention using glass/β-TCP is free-form fabrication (or rapid prototyping). In this method, TCP is usually laser-sintered with or without polymers used as additives, which polymers are also burnt completely at a later stage. In addition, the glass is incorporated as a sintering aid in the present case.

DETAILED DESCRIPTION OF THE INVENTION

The invention will hereinafter be explained in more detail by means of examples. All amounts are in percent by weight unless indicated otherwise.

EXAMPLE 1

Beta-TCP is produced according to any of the methods described in the relevant literature. The aforesaid β-TCP is ground so that a powder suitable for sintering and having a particle diameter $D_{50}$ of approx. 1.7 μm is obtained.

A material composed of (in % by weight) 74.97 $SiO_2$, 9.22 MgO and 15.81 $Na_2O$ (melted as 27.04 $Na_2CO_3$) is produced by means of a melting process. The aforesaid constituents are melted and the product obtained by the melting process is ground to obtain a powder whose particle diameter $D_{50}$ is 1.23 μm.

Subsequently, 94% by weight of the β-TCP produced and 6% by weight of the product obtained by the melting process are mixed so that a solid-state mixture is obtained, 41.68 g of a mixture of isopropanol and water (30:70) is mixed with 0.57 g disperser CE 64 and 57.75 g of said solid-state mixture and mixed in a planetary mill for 3 minutes to obtain a cream-like slurry. The slurry obtained in this way is applied onto open-pore PUR sponges whose porosity ranges between 80 and 20 ppi (pores per inch) by repeatedly immersing and squeezing the sponges, dried in air, dried in a drying chamber at approx. 100° C. for 2 hours and then slowly heated up to 1,300° C. at a rate of 100° C. per hour and held at this temperature for 6 hours. The result is a spongiosa-like product the structure of which resembles that of the sponge used, while the PUR sponge has burnt completely.

Beta-TCP is the only crystal phase which can be detected using roentgenographic analyses; its structure corresponds to that of the sponge used, it is very stable, i.e. no parts of the structure crumble away, and the resorbability of the moulded body is equal to that of β-TCP produced according to known methods.

EXAMPLE 2 (COMPARATIVE EXAMPLE)

Beta-TCP is produced in the usual manner, applied onto a PUR sponge according to the sponge impregnation technique and sintered at 1,300° C. in the same way as in Example 1. The moulded body obtained by the sintering process clearly crumbles away at several points once it has cooled down, which crumbling continues in case of mechanical contact.

EXAMPLE 3

Processing is done as in Example 1 except that the glass used is composed as follows: 71.5% $SiO_2$; 9.5% MgO; 19.0% $Na_2O$.

The aforesaid glass composition was melted, fritted and ground to obtain a powder whose particle diameter $D_{50}$ is 1.43.

EXAMPLE 4

A glass according to Example 1 is produced. Then, 9% of the aforesaid glass is mixed with 91% β-TCP. A slurry is produced by combining 30 g of the powder mixture obtained in this way with 30 ml of a 5% aqueous polyethylene glycol solution (MW: 2000) and adding 750 μl isopropyl alcohol while 0.3% of a disperser (CE 64, manufactured by Schimmer & Schwartz) is used to increase the amount of solid matter contained in the slurry. The aforesaid mixture is treated in a homogenizer (16,000 rpm; manufactured by Heidolph) for 2 minutes in order to mix it more thoroughly.

The invention claimed is:

1. An open-pore moulded body based on β-tricalcium phosphate, wherein said moulded body has a composition ranging between (in % by weight) 46.1 and 54.0 CaO, 38.9 and 45.5 $P_2O_5$, 0.005 and 11.4 $SiO_2$, 0.001 and 4.05 $Na_2O$ and 0.0005 and 1.8 MgO and solely comprises β-tricalcium phosphate as a crystalline phase according to roentgenographic analyses.

2. An open-pore moulded body based on β-tricalcium phosphate (β-TCP), wherein said moulded body has a composition ranging between (in % by weight) 46.1 and 54.0 CaO, 38.9 and 45.5 $P_2O_5$, 0.005 and 11.4 $SiO_2$, 0.001 and 4.05 $Na_2O$ and 0.0005 and 1.8 MgO and solely comprises β-tricalcium phosphate as a crystalline phase according to roentgenographic analyses and is manufactured by (a) separately producing β-tricalcium phosphate and separately producing a glass consisting of 68–78% by weight $SiO_2$, 5–12% by weight MgO and 12–27% by weight $Na_2O$,
(b) mixing 99.5–85% by weight β-tricalcium phosphate and 0.5–15% by weight glass,
(c) processing the mixture into a slurry,
(d) impregnating said slurry onto an open-pore sponge and
(e) sintering the product of step (d) at between 1,150 and 1,350° C. to obtain after cooling the moulded body, with the provision that the sintered product has β-TCP grains with a grain size of 1–7.5 μm, glass grains with a grain size of 0.7–2 μm, and with the further provision that the grain size of β-TCP must not be smaller than that of the glass.

* * * * *